United States Patent
Narula et al.

(10) Patent No.: US 8,168,163 B2
(45) Date of Patent: May 1, 2012

(54) [(4E, 4Z)-5-METHOXY-3-METHYL-4-PENTENYL]-BENZENE AND ITS USE IN PERFUME COMPOSITIONS

(75) Inventors: Anubhav P. S. Narula, Hazlet, NJ (US); Edward Mark Arruda, Easton, PA (US)

(73) Assignee: International Flavors & Fragrances, Inc., New York, NY (US)

( * ) Notice: Subject to any disclaimer, the term of this patent is extended or adjusted under 35 U.S.C. 154(b) by 351 days.

(21) Appl. No.: 12/637,827

(22) Filed: Dec. 15, 2009

(65) Prior Publication Data

US 2011/0142783 A1    Jun. 16, 2011

(51) Int. Cl.
*C07C 43/164* (2006.01)
*A61K 8/33* (2006.01)
*C11D 3/50* (2006.01)
*A61L 9/01* (2006.01)

(52) U.S. Cl. ......... 424/76.2; 568/626; 512/25; 510/102; 514/772

(58) Field of Classification Search ........................ None
See application file for complete search history.

(56) References Cited

U.S. PATENT DOCUMENTS

2007/0053860 A1*    3/2007    Eh et al. ...................... 424/70.2

OTHER PUBLICATIONS

CAPLUS abstract of WO 2005037243, published Apr. 28, 2005, which is equivalent to US 20070053860.*
Ishikawa, Y. et al. "Molecular Orbital Approach to Odor Molecules: Normal Fatty Acids and Cyclamenaldehydes." Int. J. Quantum Chem. (2000) 79(2): 101-108.
Ohloff, G. et al. "Conformationally Controlled Odor Perception in 'Steroid-type' Scent Molecules." Helvetica Chimica Acta (1983) 66(5): 1343-1354.

* cited by examiner

*Primary Examiner* — Rosalynd Keys
(74) *Attorney, Agent, or Firm* — Elizabeth M. Quirk; XuFan Tseng; Joseph F. Leightner

(57) ABSTRACT

The present invention is directed to a novel compound, [(4E, 4Z)-5-methoxy-3-methyl-4-pentenyl]-benzene, and a method of improving, enhancing or modifying a fragrance formulation through the addition of an olfactory acceptable amount of this novel compound.

9 Claims, No Drawings

[(4E,4Z)-5-METHOXY-3-METHYL-4-PENTENYL]-BENZENE AND ITS USE IN PERFUME COMPOSITIONS

FIELD OF THE INVENTION

The present invention relates to a new chemical entity and its incorporation and use as a fragrance material.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how small differences in chemical structures can result in unexpected and significant differences in odor, notes and characteristics of molecules. These variations allow perfumers and other persons to apply new compounds in creating new fragrances. For example, benzene compounds that differ slightly in substituents possess completely different odor profiles [Ishikawa, et al., International Journal of Quantum Chemistry 79: 101-108 (2000)]. In the case of tert-butyl cyclohexanes, the odor is said to be dependent on the compounds' conformation and therefore analogs adopting same conformation possess similar odor. Accordingly, many trans-compounds are shown to share pronounced urine-perspiration-type odor, while the corresponding cis-compounds are odorless or at the most possess weak and undefinable flowery or woody odor. However, some other trans- and cis-tert-butyl cyclohexanes are shown to possess opposite sensory activities [Ohloff, et al., Helvetica Chimica Acta 66, Fasc. 5: 1343-1354 (1983)]. Thus, it is hard for those with skill in the art to predict a given structure would be effective in sensory activities. Identifying desirable fragrance chemicals continues to pose difficult challenges.

SUMMARY OF THE INVENTION

The present invention provides a novel compound and its unexpected advantageous use in enhancing, improving or modifying the fragrance of perfumes, colognes, toilet waters, fabric care products, personal products and the like.

More specifically, the present invention is directed to a novel compound, [(4E,4Z)-5-methoxy-3-methyl-4-pentenyl]-benzene, which exhibits unexpected strong and unique fragrance effect and a method of improving, enhancing or modifying a fragrance formulation through the addition of an olfactory acceptable amount of [(4E,4Z)-5-methoxy-3-methyl-4-pentenyl]-benzene represented by Formula I set forth below:

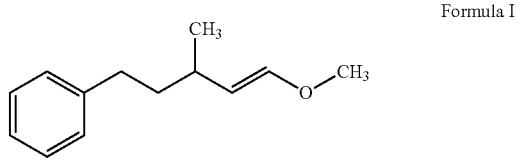

Formula I

These and other embodiments of the present invention will be apparent by reading the following specification.

DETAILED DESCRIPTION OF THE INVENTION

The compound of the present invention can be prepared from 3-methyl-5-phenyl-pentanal (commercially available from Quest International). The reaction steps can be depicted by a scheme shown as follows:

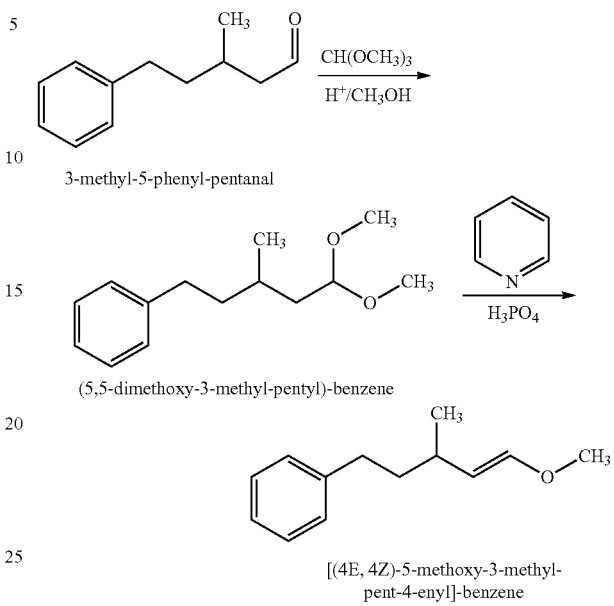

Those with skill in the art will recognize that the compounds of the present invention may have a number of chiral centers, thereby providing numerous isomers of the claimed compounds. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, and particularly gel chromatography and solid phase microextraction, referred to as SPME.

The compounds of the present invention are surprisingly found to possess strong and unexpected fragrance effect such as, for example, unique citronella, pamplemousse-like, and rhubarb-like notes.

The use of the compounds of the present invention is widely applicable in current perfumery products, including the preparation of perfumes and colognes, the perfuming of personal care products such as soaps, shower gels, and hair care products, fabric care products as well as air fresheners and cosmetic preparations. These compounds can also be used to perfume cleaning agents, such as, but not limited to detergents, dishwashing materials, scrubbing compositions, window cleaners and the like. In these preparations, the compounds of the present invention can be used alone or in combination with other perfuming compositions, solvents, adjuvants and the like. The nature and variety of the other ingredients that can also be employed are known to those with skill in the art.

Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like. A list of suitable fragrances is provided in U.S. Pat. No. 4,534,891, the contents of which are incorporated by reference as if set forth in its entirety. Another source of suitable fragrances is found in Perfumes, Cosmetics and Soaps, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

Olfactory acceptable amount is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compounds of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 10 weight percent, more preferably from about 0.5 to about 8 weight percent, and even more preferably from about 1 to about 7 weight percent. Those with skill in the art will be able to employ the desired amount to provide desired fragrance effect and intensity. In addition to the compounds of the present invention, other materials can also be used in conjunction with the fragrance formulation. Well known materials such as surfactants, emulsifiers, polymers to encapsulate the fragrance can also be employed without departing from the scope of the present invention.

When used in a fragrance formulation, the compounds of the present invention provide unexpected strong green, floral, rosy, citronella, pamplemouse-like, and rhubarb-like characteristics and make the fragrance formulation more desirable and noticeable. The odor qualities found in the compound of the present invention assist in beautifying and enhancing the finished accord and improve the performance of other materials in the fragrance formulation.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, g is understood to be gram, and mmHg be millimeters (mm) of mercury (Hg). IFF as used in the examples is understood to mean International Flavors & Fragrances Inc., New York, N.Y., USA.

EXAMPLE I

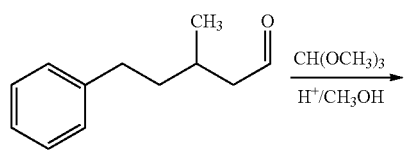

3-methyl-5-phenyl-pentanal

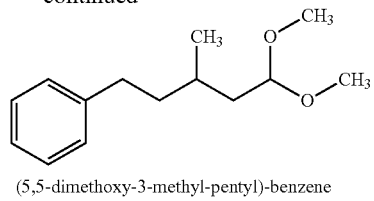

(5,5-dimethoxy-3-methyl-pentyl)-benzene

Preparation of (5,5-Dimethoxy-3-Methyl Pentyl)-Benzene: A 3 L reaction flask was fitted with a mechanical stirrer, thermometer adapter, thermometer, reflux condenser, and nitrogen inlet. The reaction flask was placed in a dry ice-IPA bath. With stirring, the flask was charged with 3-methyl-5-phenyl-pentanal (704 g, commercially available from Quest International), trimethyl orthoformate ($CH(OCH_3)_3$, 424 g, commercially available from Sigma-Aldrich Corp), and methanol ($CH_3OH$, 640 g). The pot temperature was then cooled to −20° C. and HCl (3 g) was added. An exothermic reaction occurred and the pot temperature was between 30-40° C. The dry ice-IPA bath was removed and the reaction mass was heated to 40° C. After the reaction was completed, sodium methylate (25% in $CH_3OH$, 16 g) was added in one shot. The crude product was concentrated and filtered through a bed of celite to afford 3-methyl-5-phenyl-pentanal (927 g).

H1 NMR: 0.98 ppm (d, 3H); 1.4-1.78 ppm (2m, 5H); 2.55-2.7 ppm (m, 2H); 3.3 ppm (s, 6H); 4.6 ppm (d, 1H); 5.9 ppm (d, 1H); 7.15-7.3 ppm (m, 5H).

EXAMPLE II

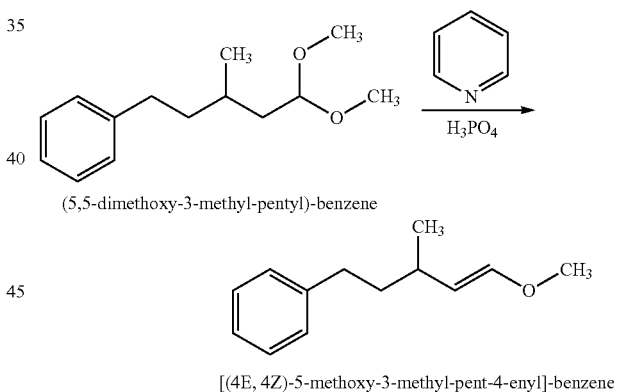

(5,5-dimethoxy-3-methyl-pentyl)-benzene

[(4E, 4Z)-5-methoxy-3-methyl-pent-4-enyl]-benzene

Preparation of [(4E,4Z)-5-Methoxy-3-Methyl-4-Pentenyl]-Benzene: A 1 L reaction flask was fitted with a mechanical stirrer, 2 inch splash column, straight take-off still head, fraction cutter with receiver, thermo well, thermocouple, nitrogen inlet, and an addition funnel. An electronic temperature controller in conjunction with a heating mantle were used for heating. From the fraction cutter a dry ice trap was connected then to a vacuum. To the nitrogen inlet a mineral oil bubbler was attached to monitor the inlet flow. While slowly stirring, the pot was charged with pyridine (4 g, commercially available from Sigma-Aldrich Corp) and phosphoric acid ($H_3PO_4$, 2 g). The reaction mass was stirred for five minutes and mixed well. The reaction pot was heated above 190° C. and 3-methyl-5-phenyl-pentanal (600 g, prepared as above in Example I) was added. After the reaction was completed, the crude product was distilled to afford [(4E,4Z)-5-methoxy-3-methyl-4-pentenyl]-benzene with a 4E:4Z isomeric ratio of 55:45 (534 g). The product compound had a boiling point of 89° C. at a pressure of 1.2 mmHg.

H1 NMR: 1.0 ppm (d, 3H); 1.5-1.7 ppm (m, 2H); 2.1-2.7 ppm (m, 4H); 3.55 ppm (s, 3H); 4.2 ppm (d, 1H); 5.9 ppm (d, 1H); 7.15-7.3 ppm (m, H).

[(4E,4Z)-5-Methoxy-3-methyl-4-pentenyl]-benzene was described as having strong green, floral, rosy, and unique citronella, pamplemouse-like, and rhubarb-like notes.

EXAMPLE III

The fragrance formula exemplified as follows demonstrates that [(4E,4Z)-5-methoxy-3-methyl-4-pentenyl]-benzene imparts green, floral, rosy, citronella, pamplemouse-like, and rhubarb-like characters to a fragrance formula.

| Ingredients | Parts* + | Parts* − |
|---|---|---|
| Phenyl eth alc white extra | 620 | 620 |
| Citronellol Coeur | 200 | 200 |
| Geraniol Coeur | 70 | 70 |
| Linalool syn | 25 | 25 |
| Phen eth acet | 20 | 20 |
| Patchouli oil light BLO | 20 | 20 |
| Ionone alpha | 10 | 10 |
| Aid C-11 ULENIC GIV 10% DPG | 8 | 8 |
| Eugenol Trubeck | 5 | 5 |
| Rose oxide 10% DPG | 5 | 5 |
| Phen Acetald 10% DEP | 2 | 2 |
| [(4E,4Z)-5-methoxy-3-methyl-4-pentenyl]-benzene | 5 | — |
| DPG | — | 5 |
| Total | 990 | 990 |

*"+" represents a [(4E,4Z)-5-methoxy-3-methyl-4-pentenyl]-benzene containing formula; and "−" represents a [(4E,4Z)-5-methoxy-3-methyl-4-pentenyl]-benzene non-containing formula.

What is claimed is:

1. A compound, [(4E,4Z)-5-methoxy-3-methyl-4-pentenyl]-benzene.

2. A method of improving, enhancing or modifying a fragrance formulation through the addition of an olfactory acceptable amount of [(4E,4Z)-5-methoxy-3-methyl-4-pentenyl]-benzene.

3. The method of claim 2, wherein the fragrance formulation is incorporated into a product selected from the group consisting of a perfume, a cologne, a toilet water, a cosmetic product, a personal care product, a fabric care product, a cleaning product, and an air freshener.

4. The method of claim 3, wherein the cleaning product is selected from the group consisting of a detergent, a dishwashing composition, a scrubbing compound, and a window cleaner.

5. The method of claim 2, wherein the olfactory acceptable amount is from about 0.005 to about 10 weight percent of the fragrance formulation.

6. The method of claim 2, wherein the olfactory acceptable amount is from about 0.5 to about 8 weight percent of the fragrance formulation.

7. The method of claim 2, wherein the olfactory acceptable amount is from about 1 to about 7 weight percent of the fragrance formulation.

8. A fragrance formulation containing an olfactory acceptable amount of [(4E,4Z)-5-methoxy-3-methyl-4-pentenyl]-benzene.

9. A fragrance product containing an olfactory acceptable amount of the compound of claim 1.

* * * * *